(12) United States Patent
Morse

(10) Patent No.: US 6,210,381 B1
(45) Date of Patent: Apr. 3, 2001

(54) SPLASH-SHIELD AND RELATED FLUID DELIVERY DEVICE

(76) Inventor: Jeffrey W. Morse, 27905 195th Ave. SE., Kent, WA (US) 98042

( * ) Notice: Subject to any disclaimer, the term of this patent is extended or adjusted under 35 U.S.C. 154(b) by 0 days.

(21) Appl. No.: 09/415,173

(22) Filed: Oct. 8, 1999

(51) Int. Cl.$^7$ ................................................ A61M 35/00
(52) U.S. Cl. .......................................... 604/289; 604/313
(58) Field of Search .................................. 604/35, 73, 187, 604/192, 268, 294, 289, 290, 295, 301, 302, 300, 164.08

(56) References Cited

U.S. PATENT DOCUMENTS

| | | | |
|---|---|---|---|
| 452,131 | 5/1891 | Haughawout | 604/289 |
| 517,274 | 3/1894 | Gollings | 604/289 |
| 603,815 | 5/1898 | Duke . | |
| 1,080,395 | 12/1913 | Wilde . | |
| 1,114,561 | 10/1914 | Wilde . | |
| 2,361,908 | 11/1944 | Bayers . | |
| 2,839,052 | 6/1958 | Verch et al. . | |
| 3,288,140 | 11/1966 | McCarthy . | |
| 4,692,140 | 9/1987 | Olson . | |
| 5,030,214 | 7/1991 | Spector . | |
| 5,133,701 | * 7/1992 | Han | 604/289 |
| 5,662,605 | 9/1997 | Hurwitz . | |
| 5,735,833 | 4/1998 | Olson . | |
| 5,795,324 | 8/1998 | Morse . | |
| 5,931,820 | 8/1999 | Morse . | |
| 5,941,859 | * 8/1999 | Lerman | 604/289 |

FOREIGN PATENT DOCUMENTS

| | | |
|---|---|---|
| 579437 | 10/1924 | (FR) . |
| 811802 | 4/1937 | (FR) . |
| 17293 | 8/1903 | (GB) . |

OTHER PUBLICATIONS

Pigman, Karch, et al., Splatter During Jet Irrigation Cleansing of a Wound Model: A Comparison of Three Inexpensive Devices, Annals of Emergency Medicine, vol. 22, No. 10, 1563–67 (Oct. 1993).

* cited by examiner

Primary Examiner—Anhtuan T. Nguyen
(74) Attorney, Agent, or Firm—Richard P. Gilly

(57) ABSTRACT

A splash-shield and related fluid delivery device is intended for medical irrigation or lavage of compromised areas of skin. The device includes a passage for fluid to exit into a bell. The passage exits into the bell closer to one edge of the bell, but is angled toward the other end of the bell, where there are bights defining drainage openings. The angled passage imparts a directional component to the fluid stream which, along with any available gravity drainage, encourages the irrigant to flow over the compromised area and out of the bell. The splash-shield is egg-shaped to cover a larger compromised area and to further enhance the distribution of irrigant. The rim of the bell is shaped to discourage unintended splashing of spent irrigant onto the administering personnel or the patient, while nonetheless allowing for efficient irrigation.

17 Claims, 3 Drawing Sheets

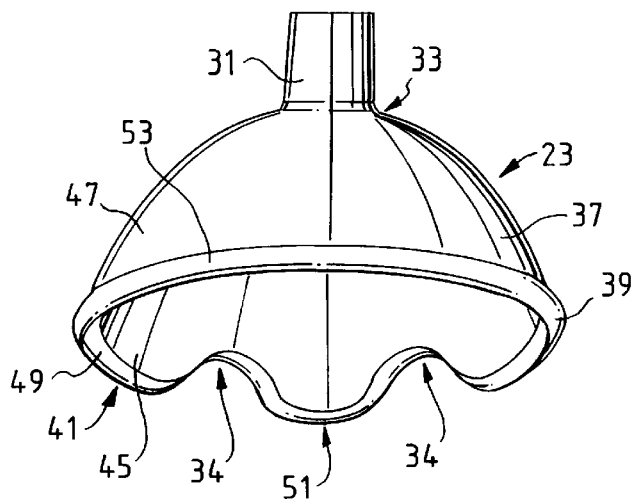
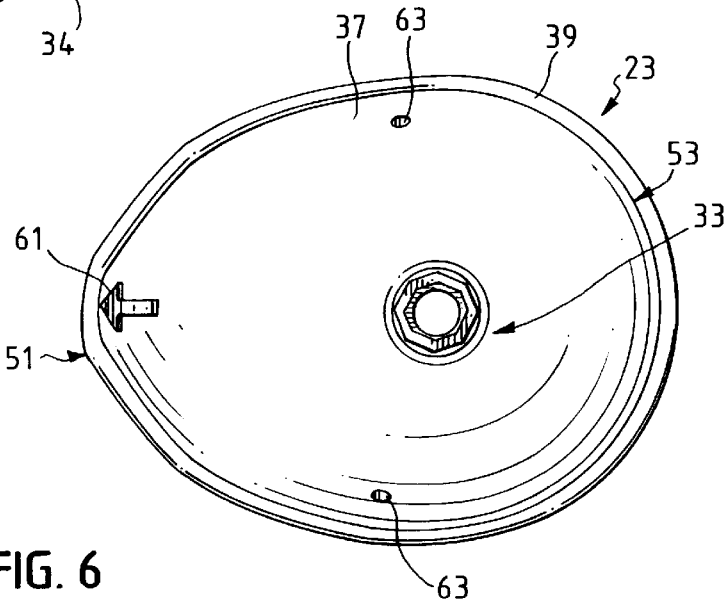
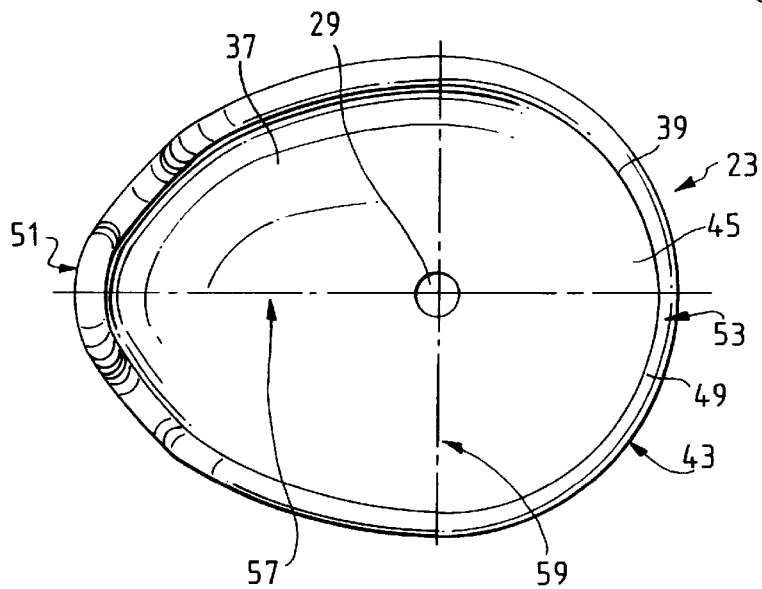

SPLASH-SHIELD AND RELATED FLUID DELIVERY DEVICE

FIELD OF THE INVENTION

This invention relates to medical devices and, more particularly, to a splash-shield and related fluid delivery device for providing effective irrigation while also preventing the splash of contaminated irrigating fluids onto administering personnel.

BACKGROUND OF THE INVENTION

Irrigation and lavage (referred to collectively as "irrigation") are commonly used in medicine to cleanse areas of the body of microscopic and macroscopic foreign contamination. Such areas of the body shall be referred to herein as "compromised areas." Such compromised areas include skin or wounds contaminated with infectious organisms, such as hepatitis virus, human immunodeficiency virus, or with biologically or chemically toxic matter. In such cases, medical personnel endeavor to remove the contaminant through copious irrigation, often with a saline solution. The fluid used to irrigate such compromised areas, the so-called "irrigant," will generally become contaminated itself after contact with and irrigation of the infected area. If this contaminated irrigant contacts other, uninfected areas of the patient, there is a risk of further infection, which is obviously undesirable.

Accordingly, there is a need to drain or remove the contaminated irrigant from unnecessary further contact with the uninfected or uncompromised areas of the patient.

There is also a risk that the contaminated irrigant will contaminate the administering medical personnel. Syringes and needles are commonly used in a variety of configurations to provide irrigation. As such, the irrigant generally exits from a fluid delivery nozzle toward the compromised area under pressure, and if the fluid stream is not properly directed, controlled, or circumscribed, the contaminated irrigant will "splash back" onto, or otherwise make unintended contact with the administering personnel. This undesirable risk of being splashed with contaminated irrigant is all the more acute when copious amounts of irrigant are used or delivered under high pressure.

There is, accordingly, a further need to protect the administering personnel from undue exposure to contaminated irrigant splashing back from the compromised area or otherwise contacting such personnel.

The syringes and needles typically used in irrigation generally do not themselves protect either the patient or administering personnel from splash back of contaminated irrigant or undesired contact therewith. The current art has attempted to overcome this disadvantage, but such attempts have there own drawbacks and disadvantages, or have been generally ineffective.

For example, administering personnel often take universal or general precautions against contamination, such as impermeable gloves, clothing barriers, eye protection, and facemasks. To assure adequate protection from such general precautions, however, they are generally combined, in hopes of synergistically enhancing protection from contamination. This approach has the disadvantage not only of greater expense, but also greater inconvenience to the administering personnel, as well as excessive time spent in taking precautionary measures.

Moreover, the use of syringes or needles risks causing further injury to soft tissue structures, such as vessels, nerves, tendons, or other subcutaneous structures often found within a wound or other compromised area during the irrigation process. In the case of sharp needles attached to a syringe for purposes of irrigation, there is also the risk of delivering irrigant at excessive pressure and thereby further damaging the area. There is likewise the risk of puncture with a contaminated needle, either to the administering personnel or the patient.

One approach to solve the above-described drawbacks and disadvantages is to provide the syringe or other fluid delivery device with a shield to prevent undesired splash back of contaminated irrigant. An example of this approach is found in U.S. Pat. No. 4,769,003 (Stamler). The shield in Stamler is designed to be tilted in proximity to the area being treated to allow drainage. One of the drawbacks of this approach, however, is that the exiting fluid stream may become, under certain circumstances, difficult to direct as desired, or may not be adequately controlled or circumscribed by the disclosed structure. Under such circumstances, it is possible for both the patient and the administering personnel to come into unnecessary contact with contaminated irrigant.

Further examples of shields on fluid delivery devices are found in U.S. Pat. No. 5,735,833 (Olson); U.S. Pat. No. 5,030,214 (Spector); and U.S. Pat. No. 4,692,140 (Olson). These approaches, however, also suffer from various drawbacks and disadvantages. For example, irrigant may be dispersed inefficiently by the structures disclosed in these references. Further, the disclosed prior art devices can be cumbersome to use in certain situations, or may likewise be cost prohibitive. As such, these devices may not be well suited for applications requiring either portability of the device, or disposal after use.

A solution is thus needed which better balances the often competing interests associated with irrigation of compromised areas of the body.

It is desirable to balance the need to cleanse the compromised area quickly and effectively, with the need to protect both the patient and the medical personnel from unnecessary contact with the irrigant.

A device is needed which delivers irrigant at sufficient volume to cleanse the area, but not at such high pressure as to damage the area.

Notwithstanding the copious volume of irrigant which may be required, a device is needed to prevent the irrigant from splashing back onto the administering personnel, but in so doing, the device should also minimize the undesirable contact of contaminated irrigant with uncontaminated areas of the patient.

Still further, it is desirable for the device to be easy to use in emergency situations, and adaptable for use with various different syringes or still other fluid delivery devices.

SUMMARY

A medical device according to the present invention delivers irrigating fluid to a wound or other compromised area of a patient and includes a splash-shield for controlling (or "circumscribing") the flow of the irrigant to minimize undesired contact with spent or contaminated irrigant, especially irrigant that splashes off of the area being irrigated. The structure of the splash-shield which circumscribes the flow of irrigant keeps the spent or contaminated irrigant away from not only the administrating personnel, but also the patient. A bell on the splash-shield has a proximal and a distal end, and the bell terminates in a rim with a rounded lip formed thereon. A fitting is formed at the proximal end of the bell, and the fitting is designed with a passage therein to receive the exit end of a fluid delivery device. The passage extends through the surface of the bell at an angle relative to the plane of the rim. At least one, preferably two bights are formed in the rim of the bell to define a corresponding drainage opening or openings.

In one version of the invention, the rim can be thought of as having a leading edge and a trailing edge opposite the leading edge. The passage exits at a location on the inner surface of the bell which is closer to the trailing edge than the leading edge, and the passage is oriented toward the leading edge. The drainage opening, in contrast, is located on the opposite leading edge. In this way, the fluid exiting the passage, although directed at the compromised area for irrigation purposes, also has a directional component toward the leading edge. This directional component toward the drainage openings is thought to improve the efficacy of irrigation and encourage drainage of spent irrigant through the drainage opening.

In accordance with another aspect of the invention, the bell has a radius increasing from the proximal end to the distal end, but with the radius at the leading edge increasing more rapidly than the radius at the trailing edge. As such, the bell encloses a volume in the shape of a half egg, and the rim encloses an elongated, ovate or egg-shaped perimeter.

The splash-shield, in accordance with other aspects of the invention, is removably received on the exit nozzle of any of a variety of delivery devices for the irrigant. Such delivery devices have a reservoir of fluid irrigant in hydraulic communication with the exit nozzle, and a suitable structure for expelling the fluid from the nozzle.

BRIEF DESCRIPTION OF THE DRAWINGS

These and other aspects of the invention are explained by the description below, in conjunction with the drawing, in which:

FIGS. 4 through 6 are rear, top, and bottom views of the splash-shield of FIG. 1;

DESCRIPTION

Figure 1:
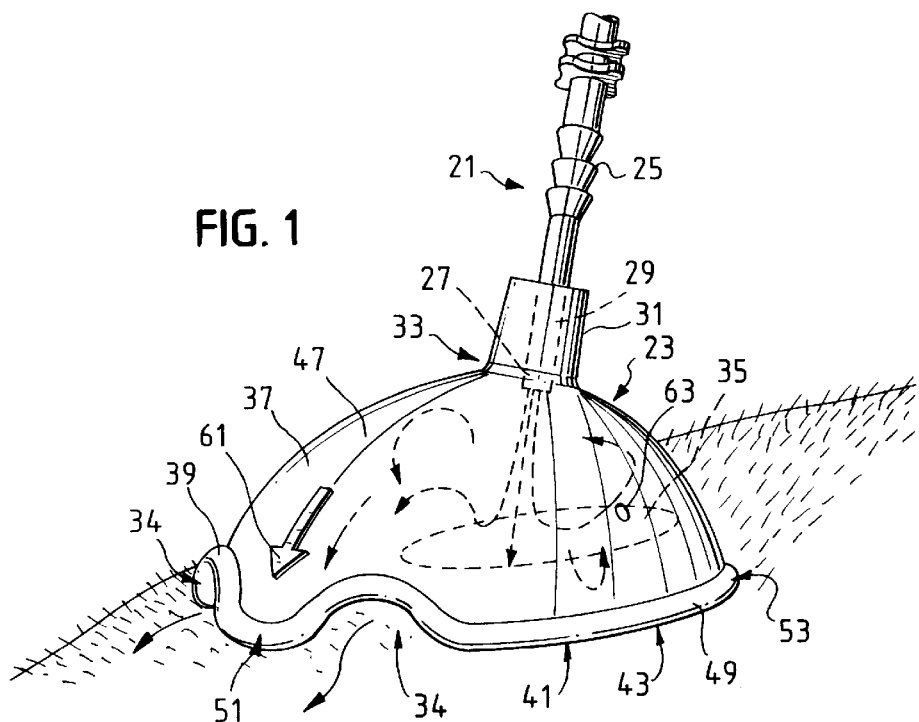
FIG. 1 is perspective view of a splash-shield according to the present invention, shown positioned over a compromised area of a patient's body to be irrigated.

Referring now to the drawing, and in particular to FIGS. 1–6, thereof, a fluid delivery device 21 of the present invention comprises a splash-shield 23 with certain structural features which control the flow of irrigating fluid, thereby keeping spent or contaminated irrigating fluid from undesired contact with either the administering personnel or the patient. In this embodiment, splash-shield 23 is shown removably mounted to a connector 25 at the exit end of a fluid delivery device, such as those shown in FIGS. 7–11. In particular, connector 25 has a nozzle end 27 which extends through a passage 29 of the splash-shield 23. The passage 29 is formed in a fitting 31 at proximal end 33 of splash-shield 23. As schematically shown in FIG. 1 by dark headed arrows, irrigating fluid exits from nozzle end 27 and irrigates compromised area 35 which is enclosed by splash-shield 23.

Passage 29 is oriented by an angle α, preferably about 15°, toward a pair of bights 34, which serve as drainage openings. The angle α of passage 29 imparts a directional component to the exiting fluid toward bights 34. Thus, although the irrigating fluid is directed toward compromised area 35 for purposes of irrigation, it also is directed toward the drainage openings. As shown in FIG. 1, splash-shield 23 is preferably positioned so that the drainage openings are downward from the compromised area 35, allowing gravity to assist in draining spent or contaminated irrigant from compromised area 35. Nonetheless, the directional component toward the drainage openings imparted by the angle α of passage 29 is also believed to encourage spent irrigant to leave the compromised area under treatment more efficiently, thereby reducing risk of either recontaminating irrigated areas or contaminating areas not under treatment. The structures of splash-shield 23 described above also allow administering personnel to better anticipate the flow of irrigant, so that such flow can be directed generally away from the administering personnel. In this way, the administering personnel are less likely to come into contact with irrigant as it drains from bights 34.

Splash-shield 23 includes additional structural features which control or circumscribe flow of irrigant, especially in regard to splash back of irrigant, and which are believed to render irrigation more efficient. Splash-shield 23 includes a bell 37 which extends from proximal end 33 in increasing radius r (FIG. 3) to terminate in rim 39 at distal end 41 of bell 37. Rim 39 defines an egg-shaped or ovate perimeter 43, best seen in FIG. 6.

Passage 29 extends between outer surface 47 of bell 37 and its inner surface 45, so that fluid can be transmitted from outside the bell 37 to the compromised area 35 enclosed by inner surface 45 of bell 37, as discussed above.

Rim 39 has a rounded lip 49 formed over substantially all its perimeter. The rounded lip has a radius sufficiently large, preferably about 3/64", to reduce the risk of damaging the already compromised area 35. For purposes of better understanding the present invention, rim 39, which extends through a 360° arc, can be divided into a leading edge 51 and a trailing edge 53 at opposite ends of such 360° arc. It is to be understood that the terms "leading" or "trailing" are not intended to limit such rim locations to particular orientations or functions relative to the compromised area 35, as such orientations or functions will vary depending on the particular compromised area 35 being treated, as well as the sound judgment of the administering personnel operating the splash-shield 23. Passage 29 exits on inner surface 45 at a location closer to trailing edge 53 than leading edge 51, as best seen in FIG. 6.

Figure 2:
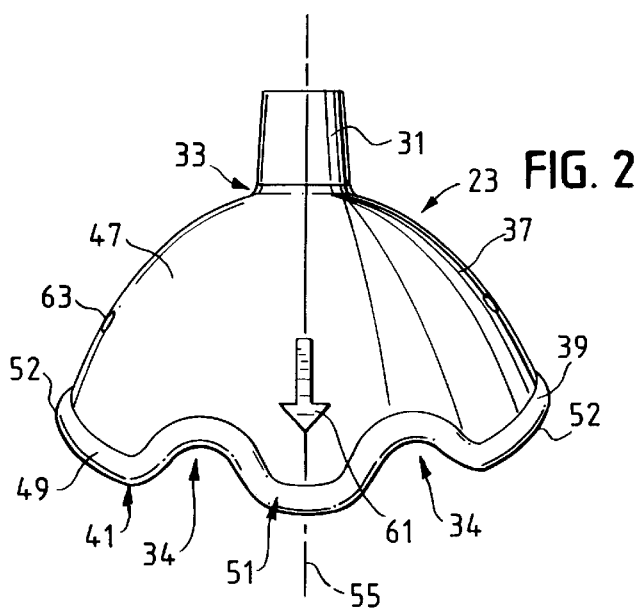
FIG. 2. is a front elevational view of the splash-shield of FIG. 1.
Figure 3:
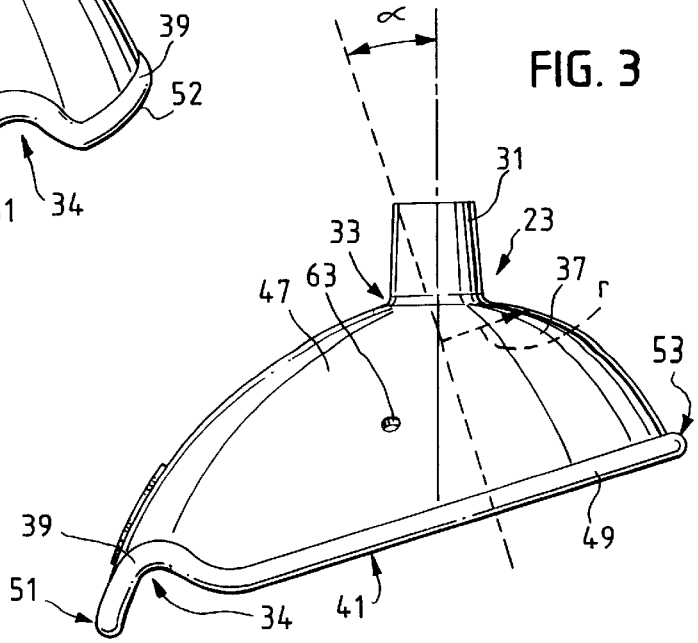
FIG. 3 is a side elevational view of the splash-shield of FIG. 1.

Bell 37 is symmetrical about a longitudinal plane 55 (FIG. 2). Passage 29 lies in longitudinal plane 55. The bights 34 are located on respective sides of longitudinal plane 55, and rim 39 has sides 52 extending substantially in a single plane from trailing edge 53 to respective ones of the bights 34.

Radius r of bell 37 increases more rapidly at arcuate locations corresponding to leading edge 51 than at corresponding locations of the trailing edge, with the result that bell 37 encloses a volume in the shape of a half egg. Rim 39 can be thought of as having a major longitudinal axis 57 which extends between leading edge 51 and trailing edge 53, and a minor transverse axis 59 perpendicular to major axis 57. Major axis 57 is longer than minor axis 59, so that bell 37 is elongated in the dimension between the leading and trailing edges 51, 53, and the corresponding area of the body enclosed by bell 37 and subject to treatment is correspondingly lengthened and thereby enlarged.

The angle of passage 29 causes fluid to exit nozzle 27 not only downwardly toward compromised area 35, but also in the elongated, longitudinal direction of bell 37 and toward the drainage openings. The lengthened area enclosed by rim 39, the location of the passage 29 toward the trailing edge 53, its angular orientation both toward the leading edge 55 and along the major, longitudinal axis, and the half-egg volume enclosed by bell 37, are believed to efficiently distribute irrigant over the compromised area 35 enclosed by rim 39, and are likewise believed to allow for efficient drainage of such irrigant through bights 34.

In operation, of course, components of the fluid stream rebound from compromised area 35 not only toward the drainage openings, but in other random directions as well. The substantially planar sides 52 of rim 39, and the coplanar trailing edge 53, allow splash-shield 23 to be brought into substantial contact with the surface of the compromised area 35 during irrigation. The rounded lip 49 permits rim 39 to be brought into contact with, or close proximity to the area 35 being treated under most situations. The fluid rebounding in random directions is inhibited from exiting the volume enclosed by bell 37 by the contact of the planar sides 52 and trailing edge 53 with the surface of the area being treated. In this way, the administering personnel and the patient is spared undesired contact by spent irrigant.

Outer surface 47 has indicia located toward leading edge 51 along axis 57 for indicating the position of the fluid stream exiting passage 29 relative to the compromised area 35. In this embodiment, such indicia comprise a raised region in the form of an arrow 61. Outer surface 47 is also provided with means for assisting the administering personnel in placing his or her fingers on splash-shield 23 to hold bell 37 in position, such means here shown as a pair of protrusions 63 located on opposite sides of bell 37 between the leading and trailing edges 51, 53.

Splash-shield 23 is preferably molded from clear, polymeric material suitable for medical devices, to enable administering personnel to visualize the fluid stream with respect to the compromised area 35. Although the exact dimensions of the structural features of the splash-shield 23 may be varied to suit different applications, in the preferred embodiment, the major, longitudinal axis 57 extends about 2 inches and the minor, transverse axis 59 is about 1.5 inches. Though the rim 39 lies preferably in a single plane with the exception of the bights 34, the present invention is not limited thereto. The bights 34 are positioned at about 40° from the longitudinal plane and have radii of about 0.25 inches. The passage 29 exits on inner surface 45 of bell 37 at a height above rim 39 of between about 0.75 inches to about 1 inch. Passage 29 is tapered from a diameter of about 17/64 of an inch to about 11/64 of an inch, to enable friction fit of nozzle end 27 in a variety of forms as discussed below.

Referring now to FIGS. 7–11, a splash-shield is part of a medical device according to the present invention for irrigating compromised areas 35. Such medical devices as shown in FIGS. 7–11 and described herein are preferably portable, suitable for irrigation under emergency department conditions, and include a reservoir of fluid irrigant, a fluid exit nozzle or tube, a splash shield mounted to such nozzle, and suitable structures to expel the fluid from the reservoir through the nozzle or exit end of the tube.

Figure 7:
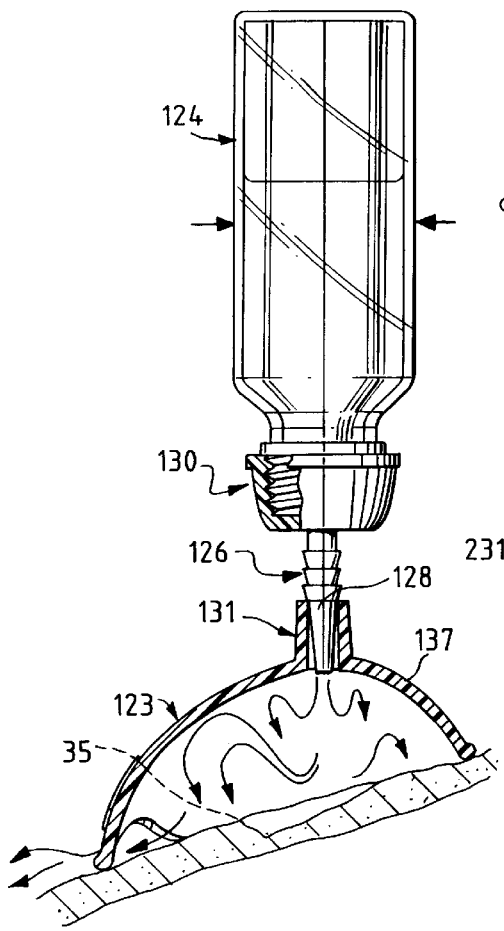
FIGS. 7 through 11 are cross-sectional views of portable medical devices according to the present invention in combination with the splash-shield of FIGS. 1–6.

In one preferred embodiment shown in FIG. 7, a squeeze bottle 124 includes a delivery fitting 126 with one connector side mounted to a cap 130 of the bottle 124 and a second, opposite male connector 128 received in a friction fit into fitting 131 of bell 137 of splash-shield 123, which splash-shield has the structural features described and shown in FIGS. 1–6. The delivery fitting 126, bottle 124, and cap 130 are further described in U.S. Pat. No. 5,795,324 issued to the same inventor, and the teachings of such disclosure are incorporated herein by reference.

Figure 8:
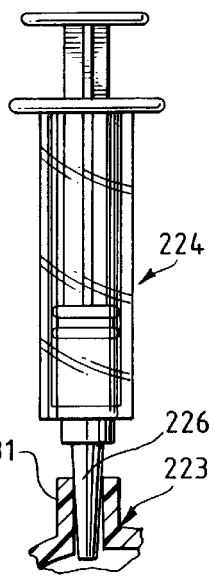
Figure 9:
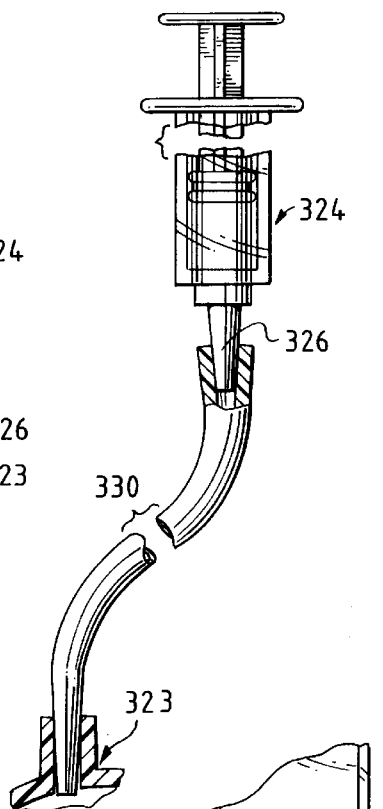

A second embodiment of a fluid delivery device of the present invention is shown in FIG. 8, in which a syringe 224 has a blunt nose 226 received into fitting 231 of splash-shield 223, which splash-shield has the structural features previously described and shown in FIGS. 1–6. FIG. 9 shows a further variation, in which an extension tube 330 is connected between the blunt nose 326 of syringe 324 and splash-shield 323. This variation allows for more flexible placement of splash-shield 323 in relation to syringe 324, as may be needed, for example, to treat compromised areas (not shown) which are less accessible or inconveniently located in relation to the administering personnel.

Figure 10:
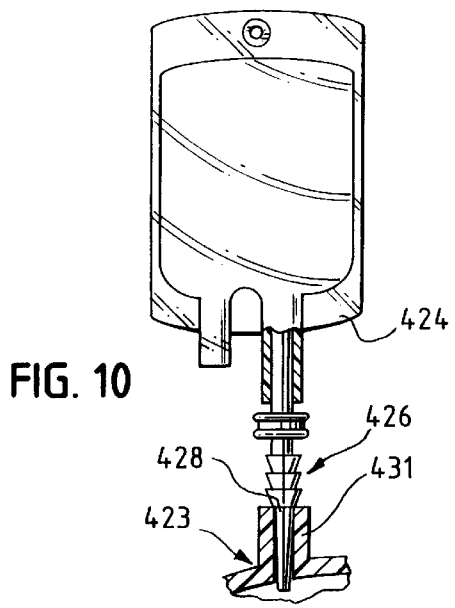
Figure 11:
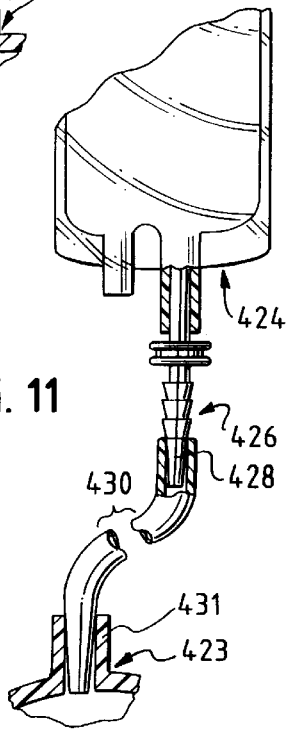

Still further embodiments of the present invention are shown in FIGS. 10 and 11. One end of delivery fitting 426 is a male-type connector adapted to "spike" into an IV bag 424. The other end of delivery fitting 426 is a male-type connector adapted to frictionally insert into fitting 431 of splash-shield 423 in the case of FIG. 10, or into the appropriate end of extension tubing 430 in the case of FIG. 11. The structure and use of delivery fitting 426 is further described in U.S. Pat. No. 5,931,820 issued to the same inventor, and its teachings are incorporated herein by reference.

Operation of the splash-shield and associated fluid delivery device is readily apparent from the foregoing description. A suitable configuration of fluid reservoir is selected, and an appropriate connector with or without extension tubing is interconnected between the fluid reservoir and the splash-shield. The administering personnel place the splash-shield against or very close to the compromised area to be treated. The splash-shield is preferably oriented so that drainage through bights 34 is gravity-assisted and, where possible, so that the flow of irrigant is away from the administering personnel. Fluid exiting splash shield 23 through bights 34 may be contained by absorbent material such as towels or collected by a suitable container. The portability of the device obviously allows the splash-shield to be applied in any orientation so as to substantially enclose the compromised area to be treated.

Once the splash-shield has been appropriately positioned, the administering personnel expels the fluid as appropriate to the particular situation, typically saline solution, by whatever means are appropriate to the fluid reservoir selected, namely, movement of a plunger in the case of a syringe, or squeezing the flexible sides of a squeeze bottle or IV bag.

In addition to the advantages apparent from the foregoing description, the fluid delivery device of the present invention accomplishes efficient irrigation or lavage, while at the same time minimizing undesired contact of the administering personnel or patient with spent or contaminated irrigant. In particular, the device minimizes "splashing" of the irrigant outside the treatment area.

The splash-shield can be advantageously placed against most compromised areas with less risk of further compromising the area.

As still another advantage, the irrigation device is cost effective and easy to operate quickly, such as may be required in emergency interventions.

The present invention has been described with reference to particular preferred embodiments. Such description is for purposes of setting out the best mode of practicing the invention for one skilled in the art, and is not intended to limit the invention to the particular instrumentalities disclosed. Still further variations to the described invention may be appreciated by those skilled in the art, or as skill or fancy may suggest, the invention thus being defined only by the appended claims and encompassing equivalent structures thereto.

What is claimed is:

1. A splash-shield for use at the exit end of a fluid delivery device to irrigate a compromised area of the body, such as a wound, the splash-shield comprising:
   a bell having proximal and distal ends, and inner and outer surfaces extending from the proximal end to terminate in a rim at the distal end, the rim defining an egg-shaped perimeter;
   a rounded lip formed along the rim, the rounded lip having a radius sufficiently large to minimize damage to the compromised area;
   a fitting formed in the proximal end of the bell, the fitting having a passage extending between the inner and outer surfaces, the passage oriented at an oblique angle to a plane corresponding to the rim, the passage sized to receive the exit end of the fluid delivery device therein; and
   at least one bight formed in the rim of the bell to define a corresponding drainage opening in the rim.

2. The splash-shield of claim 1, wherein the rim comprises a leading edge and a trailing edge opposite the leading edge, wherein the passage exits at a location on the inner surface closer to the trailing edge than the leading edge, wherein the angle orients the passage toward the leading edge, and wherein the drainage opening is located on the leading edge, whereby fluid exiting the passage has a directional component toward the leading edge.

3. The splash-shield of claim 2, further comprising a pair of the bights defining two of the drainage openings, wherein the bell is symmetrical about a longitudinal plane therethrough, wherein the passage lies in the longitudinal plane, wherein respective ones of the bights lie on either side of the longitudinal plane, wherein the rim has a pair of sides extending substantially in a single plane from the trailing edge to respective ones of the bights, so that, when the sides are in contact with the surface of the compromised area being treated, such contact inhibits fluid from splashing transversely out of the bell.

4. The splash-shield of claim 3, wherein the outer surface at the leading edge has indicia longitudinally aligned with the passage to indicate the position of the fluid exiting the passage relative to the compromised area so as to assist an irrigator in proper placement of the fluid stream relative to the compromised area to be irrigated.

5. The splash-shield of claim 4, wherein the indicia comprise a raised region visible to the eye and formed in the outer surface.

6. The splash-shield of claim 2, further comprising means for guiding the fingers of the user to optimal positions to hold the bell in position.

7. The splash-shield of claim 6, wherein the means comprises a pair of protrusions from the outer surface of the bell located on opposite sides of the bell between the leading and trailing edges.

8. The splash-shield of claim 2, wherein the bell has a radius increasing from the proximal end to the distal end.

9. The splash-shield of claim 8, wherein the radius at the leading edge increases more rapidly than the radius at the trailing edge, whereby the bell encloses a volume in the shape of a half egg.

10. The splash-shield of claim 2, wherein a major longitudinal axis extends between the leading edge and the trailing edge, and a minor transverse axis extends perpendicular to the major axis, and wherein the major axis is longer than the minor axis, so that the bell is elongated between the trailing edge and the leading edge, the area of the body enclosed by the bell and subject to irrigation being correspondingly lengthened and thereby enlarged.

11. The splash-shield of claim 10, further comprising a bell axis extending orthogonally to the plane of the rim, wherein the passage is angled at about 15° from the bell axis, and wherein the radius of the rim is about 3/64".

12. A portable medical device for emergency irrigation of a wound or other compromised area of a patient, the device comprising:
   a delivery device for the irrigant, the device having a reservoir of fluid irrigant, a fluid exit nozzle, and means for manually expelling the fluid from the nozzle;
   a splash-shield having a bell and a fitting defined in the bell to removably receive the exit nozzle therein, the splash-shield, delivery device, and reservoir being sized and configured to be hand-held and self-contained for use under emergency conditions;
   inner and outer surfaces extending from the proximal end of the bell to terminate in a rim at the distal end of the bell, the rim defining an egg-shaped perimeter;
   a rounded lip formed along the rim, the rounded lip having a radius sufficiently large to minimize damage to the compromised area of the patient;
   at least one drainage opening defined in a portion of the rim;
   a passage defined in the fitting and extending between the inner and outer surfaces, the passage oriented at an oblique angle to a plane corresponding to the rim to expel the fluid at a corresponding angle to the area to be treated when the rim is placed thereagainst, the passage being generally oriented toward the drainage opening so that the fluid exiting the passage generally flows over the area and substantially toward the drainage opening.

13. The device of claim 12, wherein the passage and the fluid exit nozzle removably received therein have opposing surfaces cooperating to hold the fluid exit nozzle in a friction fit and to position the tip of the nozzle inwardly of the inner surface of the bell, whereby fluid exits the nozzle substantially without impingement by the inner surface.

14. The device of claim 12, wherein the delivery device is selected from the group consisting of an IV bag and squeeze bottle, and wherein the fluid exit nozzle comprises a delivery fitting having a male connector extending from two, opposite sides, the first male connector adapted to be connected in fluid communication with the fluid reservoir, the second male connector adapted to be received in the fitting of the bell.

15. The device of claim 12, wherein the delivery device comprises a syringe.

16. The device of claim 12, wherein the rim comprises a leading edge and a trailing edge opposite the leading edge, wherein the passage exits at a location on the inner surface closer to the trailing edge than the leading edge, wherein the angle orients the passage toward the leading edge, wherein the drainage opening is located on the leading edge, wherein a major longitudinal extends between the leading edge and the trailing edge, wherein a minor transverse axis extends perpendicular to the major axis, and wherein the major axis is longer than the minor axis so that the bell is elongated between the trailing edge and the leading edge, the area of the body enclosed by the bell and subject to irrigation being correspondingly lengthened and thereby enlarged, the fluid exiting the passage with a directional component toward the leading edge to effectively irrigate the elongated area enclosed by the bell.

17. The device of claim 12, wherein the radius of the rim is about 3/64".

* * * * *